(12) United States Patent
Wu et al.

(10) Patent No.: US 9,986,963 B2
(45) Date of Patent: Jun. 5, 2018

(54) METHOD AND APPARATUS FOR REDUCING RADIATION FROM CT MEASUREMENT OF RESPIRATORY CYCLES AND CT SCANNER

(71) Applicant: GENERAL ELECTRIC COMPANY, Schenectady, NY (US)

(72) Inventors: Hai Feng Wu, Beijing (CN); Meng Zhang, Beijing (CN); Ioannis Genitsarios, Athens (GR)

(73) Assignee: General Electric Company, Schenectady, NY (US)

( * ) Notice: Subject to any disclaimer, the term of this patent is extended or adjusted under 35 U.S.C. 154(b) by 577 days.

(21) Appl. No.: 14/535,746

(22) Filed: Nov. 7, 2014

(65) Prior Publication Data

US 2015/0139384 A1    May 21, 2015

(30) Foreign Application Priority Data

Nov. 15, 2013   (CN) .......................... 2013 1 0573492

(51) Int. Cl.
| | | |
|---|---|---|
| *A61B 6/00* | (2006.01) | |
| *A61B 5/08* | (2006.01) | |
| *A61B 6/03* | (2006.01) | |

(52) U.S. Cl.
CPC ............ *A61B 6/542* (2013.01); *A61B 5/0816* (2013.01); *A61B 6/032* (2013.01); *A61B 6/541* (2013.01)

(58) Field of Classification Search
CPC ....... A61B 5/0816; A61B 6/032; A61B 6/541; A61B 6/542; A61B 5/113; A61B 5/055; A61B 5/7289; A61B 1/2676; A61B 5/7285; A61B 2017/0034; A61B 2017/00694; A61B 2017/00809; A61B 2017/22038; A61B 2017/248; A61B 2034/2051; A61B 2090/371; A61B 34/20; A61B 5/1127; A61B 6/5264; A61B 5/7257; A61B 6/0337; A61B 5/0033; A61B 5/5022; A61B 5/085; A61B 5/721; A61B 6/03; A61B 6/4458; A61B 6/5247; A61B 6/5282; A61B 6/503; A61B 6/027; A61B 6/504; A61B 6/481; A61B 6/545; A61B 6/488; A61B 6/5205; A61B 6/544; A61B 6/469; A61B 6/486; A61B 6/0457; A61B 6/06; A61B 6/4014; A61B 6/4441
USPC ................................ 378/4, 8, 19, 68, 69, 95
See application file for complete search history.

(56) References Cited

U.S. PATENT DOCUMENTS

| | | | | |
|---|---|---|---|---|
| 5,251,128 A | * | 10/1993 | Crawford ............... | A61B 5/113 600/425 |
| 7,050,537 B2 | * | 5/2006 | Tsujii ................... | A61B 6/5217 378/95 |
| 2006/0129044 A1 | * | 6/2006 | Le Corre ............. | A61N 5/1048 600/428 |
| 2007/0270689 A1 | * | 11/2007 | Lothert .................. | A61B 6/032 600/428 |

* cited by examiner

*Primary Examiner* — Irakli Kiknadze
(74) *Attorney, Agent, or Firm* — McCoy Russell LLP

(57) ABSTRACT

A method for reducing radiation from CT measurement of respiratory cycles and a corresponding CT scanner. The method includes: determining a lying direction of a patient to be measured; and setting a tube position for a first respiratory cycle measurement of the patient according to the lying direction.

20 Claims, 2 Drawing Sheets

METHOD AND APPARATUS FOR REDUCING RADIATION FROM CT MEASUREMENT OF RESPIRATORY CYCLES AND CT SCANNER

TECHNICAL FIELD

Embodiments of the present invention relate to method and apparatus for reducing X-ray radiation, and more particularly, to a method and apparatus for reducing radiation from CT measurement of respiratory cycles and a corresponding CT scanner.

BACKGROUND ART

When a CT (computed tomography) scanner is used to scan a patient's thoracic or abdominal viscera, the patient's respiration may cause distortion of CT images. To eliminate this distortion, the concept of four-dimensional CT (4D CT) was proposed. For 4D CT, it is critical to measure the patient's respiratory cycles accurately.

In the existing methods of measuring respiratory cycles with a CT scanner, a marker may be placed on the body of the patient, which marker may move with the patient's respiration, such that a respiratory cycle curve may be formulated by tracking positions of the marker via CT scans.

We find that there is still room for further reducing the radiation dose of X-rays when the above-described methods are adopted to measure respiratory curves.

Therefore, an embodiment of the present invention provides method and apparatus for reducing radiation from CT measurement of respiratory cycles and a corresponding CT scanner, such that when the CT scanner is used to track the marker for respiratory cycle measurement, the radiation dose of X-rays from the CT tube can be further lowered.

SUMMARY OF THE INVENTION

An embodiment of the present invention provides a method for reducing radiation from CT measurement of respiratory cycles, including: determining a lying direction of a patient to be measured; and setting a tube position for a first respiratory cycle measurement of the patient according to the lying direction.

Another embodiment of the present invention provides an apparatus for reducing radiation from CT measurement of respiratory cycles, including: a direction determining module for determining a lying direction of a patient to be measured; and a tube position setting module for setting a tube position for a first respiratory cycle measurement of the patient according to the lying direction.

Another embodiment of the present invention provides a CT scanner including an apparatus for reducing radiation from CT measurement of respiratory cycles. The apparatus having a direction determining module for determining a lying direction of a patient to be measured, and a tube position setting module for setting a tube position for a first respiratory cycle measurement of the patient according to the lying direction.

BRIEF DESCRIPTION OF THE DRAWINGS

The present invention will be more apparent to those skilled in the art upon reading the following detailed description of embodiments with reference to the accompanying drawings, in which.

DETAILED DESCRIPTION OF THE INVENTION

Some specific embodiments of the present invention will be described hereinafter. However, it should be noted that it is impossible to elaborate on all the features of a specific embodiment for sake of clarity and conciseness. It should be understood that in practical implementation of any embodiment, as is in any engineering or designing process, a variety of particular decisions and changes from one implementation to another would often be made, in order to achieve the developers' specific goals, or to meet system-related, or business-related constraints. It should be also understood that, although such development process may involve complicated and time-consuming endeavors, certain modifications to the design, manufacture or production on the basis of the present disclosure are nothing but conventional technical means for a skilled artisan in the related field, and the present disclosure should not be construed as being insufficient.

Unless otherwise defined, the technical terms or scientific terms used in the claims and the description should have a usual meaning generally understood by those having ordinary skills in the art to which the present invention relates. The wordings "first", "second" and the like used in the description and the claims are not intended to indicate any order, quantity, or importance, but to distinguish between different components. The words "a", "an" and the like do not mean quantitative restrictions, but presence of at least one. The words "comprising", "including" and the like mean that an element or object before these words covers an element, object or equivalents listed after these words, but do not exclude presence of other element or object. "Connect to" or "connect with" and other similar wordings are not limited to physical or mechanical connections, nor are they limited to direct or indirect connections.

To make the objects, technical solutions and advantages of the present invention more apparent, the technical solution of the present invention will be described in a clear and complete manner in combination with specific embodiments and corresponding drawings. Evidently, these embodiments are only part of, not all embodiments of the present invention. Any other embodiment obtained by a person ordinary skilled in the art without inventive labor on the basis of these embodiments will fall within the scope of the present invention.

Figure 1:
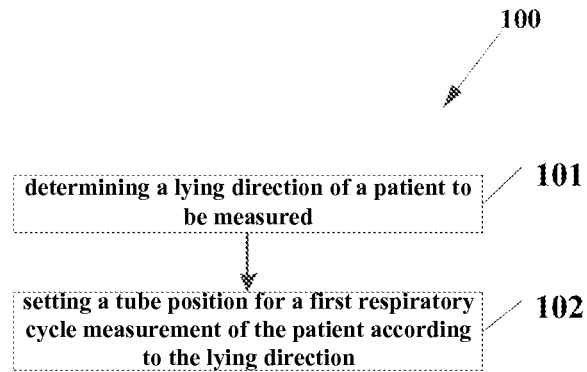
FIG. 1 is a flow diagram illustrating a method for reducing radiation from CT measurement of respiratory cycles according to one embodiment of the present invention.

Reference is made to FIG. 1, which is a flow diagram illustrating a method 100 for reducing radiation from CT measurement of respiratory cycles according to one embodiment of the present invention.

As shown in FIG. 1, a lying direction of a patient is determined in step 101.

In measuring the patient's respiratory cycles with a CT scanner, the patient normally lies in the bed of the CT scanner with a supine position. In the actual course of clinical practice, there may be two lying directions for the patient, one being the patient's head adjacent to the CT scanner gantry and the other being the patient's feet adjacent to the CT scanner gantry.

In step 102, a tube position is set for a first respiratory cycle measurement of the patient according to the lying direction.

In an embodiment of the present invention, corresponding menus or buttons may be set in the user interface of the CT scanner, which menus or buttons provide the doctor with at least two options: one being the patient's head adjacent to the CT scanner gantry (also called "head entry first"), and the other being the patient's feet adjacent to the CT scanner gantry (also called "feet entry first"). In a first respiratory cycle measurement of the patient, after determining a lying direction of the patient, the doctor can operate the menus or buttons, thereby turning the CT tube to a preset position. The preset position may be set away from an organ (such as the heart) that needs protection such that radiation exposure dose to said organ may be minimized. The preset position may also be set to balance organ protection and detection quality of the marker moving with the patient's respiration.

Figure 2:
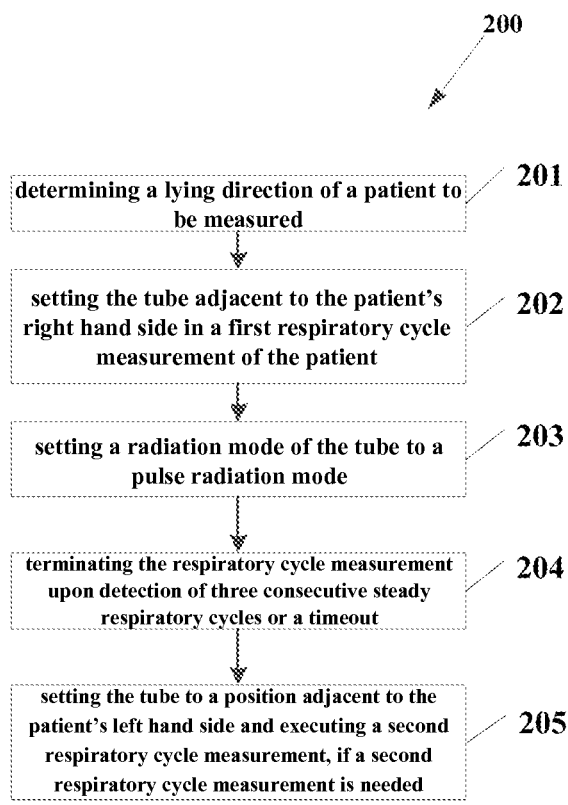
FIG. 2 is a flow diagram illustrating a method for reducing radiation from CT measurement of respiratory cycles according to another embodiment of the present invention.

Reference is made to FIG. 2, which is a flow diagram illustrating a method 200 for reducing radiation from CT measurement of respiratory cycles according to another embodiment of the present invention.

A lying direction of a patient to be measured is determined in step 201. The process of step 201 is similar to that of step 101, and thus further elaboration thereon would be unnecessary.

In step 202, the tube is set to a position adjacent to the patient's right hand side in a first respiratory cycle measurement of the patient.

According to an embodiment of the present invention, the tube may be positioned anywhere between 68-88 degrees when the patient lies in such a direction that his head is adjacent to the CT scanner gantry. More particularly, the tube is positioned at 78 degrees. The angles mentioned above and below refer to the 12 o'clock direction as zero degree.

According to an embodiment of the present invention, the tube may be positioned anywhere between 272-292 degrees when the patient lies in such a direction that his feet are adjacent to the CT scanner gantry. More particularly, the tube is positioned at 282 degrees.

Since the human heart is located in the chest and slightly on the left, i.e., at a position adjacent to the left hand side, setting the tube position adjacent to the patient's right hand side in step 202 can lower the heart's X-ray radiation exposure dose from the tube.

In step 203, the radiation mode of the tube is set to a pulse radiation mode.

According to an embodiment of the present invention, in the process of measuring respiratory cycles, the CT scanner tube may be in a continuous radiation mode, i.e., the tube continuously emits X-rays during the process of measuring respiratory cycles. More particularly, the tube may be in a pulse radiation mode in the process of measuring respiratory cycles, i.e., the tube emits X-rays in pulse. For example, the tube emits X-rays only in 2 out of 100 milliseconds, and does not emit X-rays in the rest 98 milliseconds.

Radiation dose during respiratory scan process with the CT scanner can be further lowered by virtue of the pulse radiation mode.

In step 204, upon detection of three consecutive steady respiratory cycles or a timeout, the respiratory cycle measurement will be terminated.

During the respiratory cycle measurement, controlling the total time length and judging the stability of respiratory cycles can further shorten the duration of CT measurement of respiratory cycles, and can thus further reduce the radiation dose to which the patient is exposed.

Figure 3:
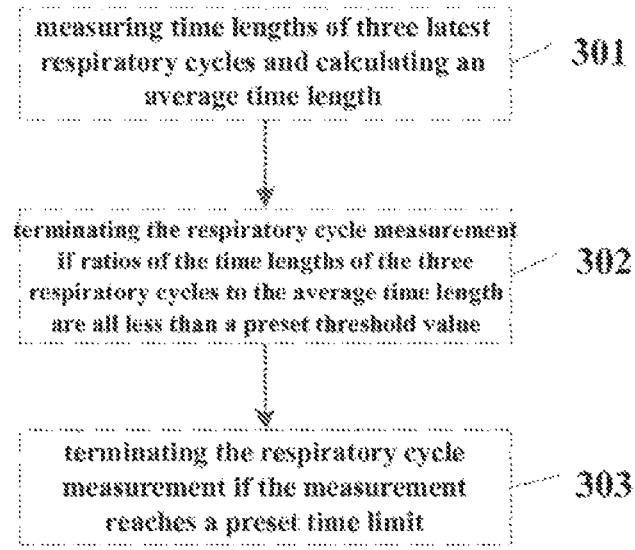
FIG. 3 is a flow diagram illustrating termination of respiratory cycle measurement upon detection of three consecutive steady respiratory cycles or a timeout in the process of reducing radiation from CT measurement of respiratory cycles according to one embodiment of the present invention.

FIG. 3 shows schematically the process of step 204 according to an embodiment, wherein step 204 includes steps 301 to 303 as follows.

In step 301, time lengths of three latest respiratory cycles are measured and an average time length is calculated.

By continuously monitoring the respiratory motion, time lengths T2, T1 and T0 of three latest respiratory cycles are measured respectively, hence the average time length Ta is obtained.

In step 302, if the ratios of the time lengths of the three respiratory cycles to the average time length are all less than a preset threshold value, the respiratory cycle measurement will be terminated.

According to an embodiment of the present invention, whether to terminate measurement of respiratory cycles may be determined in the following manner: if the maximum value among |Ta−T2|/Ta, |Ta−T1|/Ta and |Ta−T0|/Ta does not exceed a preset threshold value, it can be deemed that three consecutive steady respiratory cycles are acquired and measurement can be terminated. Otherwise, it is deemed that three consecutive steady respiratory cycles are not acquired.

In step 303, upon reaching a preset time limit, the measurement of respiratory cycles will be terminated.

According to an embodiment of the present invention, if the time length for one measurement of respiratory cycles reaches 40 seconds, this measurement of respiratory cycles may be terminated and the next measurement of respiratory cycles may be performed.

In step 205, if a second respiratory cycle measurement is needed, the tube is set adjacent to the patient's left hand side and the second measurement is executed.

One reason that the second respiratory cycle measurement is needed may be due to failure of the first measurement of respiratory cycles. In an embodiment of the present invention, the second respiratory cycle measurement may be performed after positioning the tube adjacent to the left hand side of the patient, so that a same region will not be exposed to radiation dose twice in the two respiratory cycle measurements.

Contrary to the setting in step 202, according to an embodiment of the present invention, in the second measurement of respiratory cycles, the tube may be positioned anywhere between 68-88 degrees when the patient lies in such a direction that his feet are adjacent to the CT scanner gantry. More particularly, the tube is positioned at 78 degrees.

According to an embodiment of the present invention, the tube may be positioned anywhere between 272-292 degrees when the patient lies in such a direction that his head are adjacent to the CT scanner gantry. More particularly, the tube is positioned at 282 degrees.

Likewise, if the second measurement of respiratory cycles fails, a third measurement thereof may be further needed. For this measurement, the tube may be set adjacent to the right hand side of the patient, and specifically at a position described in step 202.

Of course, in order for the patient's total radiation exposure dose to be not too large, in an embodiment of the present invention, it may be defined that there can only be three times of respiratory cycle measurement at the most. If three measurements all fail, the doctor may be reminded to take corresponding measures.

What is hitherto described is a method reducing radiation from CT measurement of respiratory cycles according to an embodiment of the present invention, via which the radiation dose to which the patient is exposed during CT measurement of respiratory cycles can be reduced, and vital organs can be protected effectively.

Figure 4:
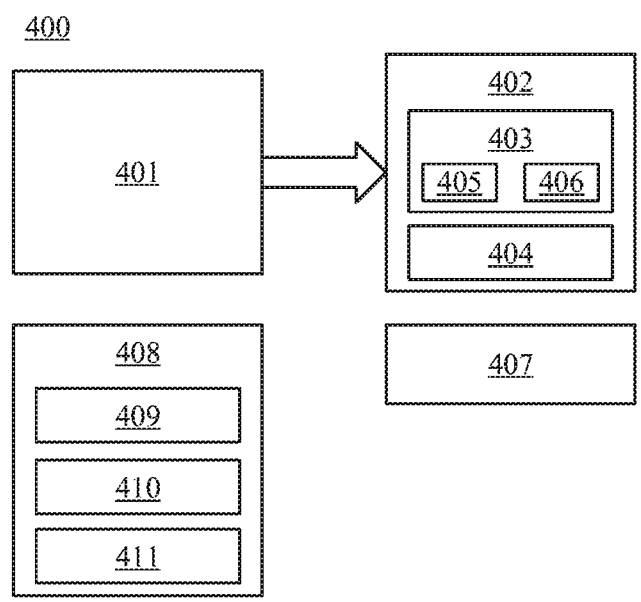
FIG. 4 is a schematic block diagram of an apparatus for reducing radiation from CT measurement of respiratory cycles according to one embodiment of the present invention.

Similar to the method described above, an embodiment of the present invention also provides a corresponding apparatus. FIG. 4 is a schematic block diagram of an apparatus for reducing radiation from CT measurement of respiratory cycles according to one embodiment of the present invention.

As shown in FIG. 4, an apparatus 400 may include: a direction determining module 401 for determining a lying direction of a patient; and a tube position setting module 402 for setting a tube position for a first respiratory cycle measurement of the patient according to the lying direction.

According to an embodiment of the present invention, the tube position setting module 402 may further include a first tube position setting module 403 for setting the tube to a position adjacent to the patient's right hand side.

According to an embodiment of the present invention, the apparatus 400 may also include a second tube position setting module 404 for setting the tube to a position adjacent to the patient's left hand side and executing a second respiratory cycle measurement, if a second respiratory cycle measurement is needed.

According to an embodiment of the present invention, the first tube position setting module 403 may further include: a module 405 for setting the tube to a position between 68-88 degrees when the patient lies in such a direction that his head is adjacent to the CT scanner gantry; and a module 406 for setting the tube to a position between 272-292 degrees when the patient lies in such a direction that his feet are adjacent to the CT scanner gantry.

According to an embodiment of the present invention, the apparatus 400 may further include a pulse radiation mode setting module 407 for setting the radiation mode of the tube to a pulse radiation mode.

According to an embodiment of the present invention, the apparatus 400 may also include a measurement terminating module 408 for terminating measurement of respiratory cycles upon detection of three consecutive steady respiratory cycles or a timeout.

According to an embodiment of the present invention, the measurement terminating module 408 may further include: an average time length calculating module 409 for measuring time lengths of three latest respiratory cycles and calculating an average time length; a judging module 410 for terminating measurement of respiratory cycles if the ratios of the time lengths of the three respiratory cycles to the average time length are all less than a preset threshold value; and a timeout interrupting module 411 for terminating measurement of respiratory cycles if the measurement reaches a preset time limit.

What is hitherto described is an apparatus for reducing radiation from CT measurement of respiratory cycles according to an embodiment of the present invention, via which the radiation dose to which the patient is exposed during CT measurement of respiratory cycles can be reduced, and vital organs can be protected effectively.

While the present invention has been described in detail with reference to specific embodiments, a skilled person will understand that the present invention is not limited to said embodiments. For those skilled in the art, various modifications and variations may be made to the present invention. Any modification, substitution, improvement or the like without departing from the spirit and principle of the present invention, shall be included in the scope of the present invention that is defined in the appending claims.

What is claimed is:

1. A method for reducing radiation from CT measurement of respiratory cycles, the method comprising:
   determining a lying direction of a patient to be measured, wherein the lying direction is a first direction or a second direction;
   setting a position of a CT tube relative to the patient for a first respiratory cycle measurement of the patient to a first position if the lying direction is the first direction;
   performing the first respiratory cycle measurement of the patient lying in the first direction with the CT tube at the first position;
   setting the position of the CT tube relative to the patient for the first respiratory cycle measurement of the patient to a second position if the lying direction is the second direction; and
   performing the first respiratory cycle measurement of the patient lying in the second direction with the CT tube at the second position.

2. The method according to claim 1, wherein setting the position of the CT tube further comprises setting the CT tube to a position adjacent to a right hand side of the patient.

3. The method according to claim 2, wherein setting the CT tube to the position adjacent to the right hand side of the patient further comprises:
   setting the CT tube anywhere between 68-88 degrees when the patient lies in such a direction that his head is adjacent to a CT scanner gantry; and
   setting the CT tube anywhere between 272-292 degrees when the patient lies in such a direction that his feet are adjacent to the CT scanner gantry.

4. The method according to claim 3, further comprising:
   setting a radiation mode of the CT tube to a pulse radiation mode.

5. The method according to claim 2, further comprising:
   setting a radiation mode of the CT tube to a pulse radiation mode.

6. The method according to claim 1, further comprising:
   when a second respiratory cycle measurement is needed, setting the CT tube to a position adjacent to the patient's left hand side and executing the second respiratory cycle measurement.

7. The method according to claim 6, further comprising:
   setting a radiation mode of the CT tube to a pulse radiation mode.

8. The method according to claim 1, further comprising:
   setting a radiation mode of the CT tube to a pulse radiation mode.

9. The method according to claim 1, further comprising:
   terminating the first respiratory cycle measurement upon detection of three consecutive steady respiratory cycles or a timeout, wherein the method further includes performing the first respiratory cycle measurement on a first patient lying in the first direction, and performing the second respiratory cycle measurement on a second patient lying in the second direction.

10. The method according to claim 9, wherein terminating the first respiratory cycle measurement further comprises:

measuring time lengths of three latest respiratory cycles and calculating an average time length;

terminating the first respiratory cycle measurement if ratios of the time lengths of the three latest respiratory cycles to the average time length are all less than a preset threshold value; and terminating the first respiratory cycle measurement if the measurement reaches a preset time limit.

11. An apparatus for reducing radiation from CT measurement of respiratory cycles, the apparatus comprising:

a direction determining module for determining a lying direction of a patient to be measured, wherein the lying direction is a first direction or a second direction;

a tube position setting module for setting a position of a CT tube relative to the patient for a first respiratory cycle measurement of the patient to a first position if the lying direction is the first direction;

performing the first respiratory cycle measurement of the patient lying in the first direction with the CT tube at the first position;

setting the position of the CT tube relative to the patient for the first respiratory cycle measurement of the patient to a second position if the lying direction is the second direction; and performing the first respiratory cycle measurement of the patient lying in the second direction with the CT tube at the second position.

12. The apparatus according to claim 11, wherein the tube position setting module further comprises a first tube position setting module for setting the CT tube to a position adjacent to the patient's right hand side.

13. The apparatus according to claim 12, further comprising:

a second tube position setting module for setting the CT tube to a position adjacent to the patient's left hand side and executing a second respiratory cycle measurement, if the second respiratory cycle measurement is needed.

14. The apparatus according to claim 13, wherein the first tube position setting module further comprises:

a module for setting the CT tube anywhere between 68-88 degrees when the patient lies in such a direction that his head is adjacent to a CT scanner gantry; and a module for setting the CT tube anywhere between 272-292 degrees when the patient lies in such a direction that his feet are adjacent to the CT scanner gantry.

15. The apparatus according to claim 11, further comprising:

a pulse radiation mode setting module for setting a radiation mode of the CT tube to a pulse radiation mode.

16. The apparatus according to claim 11, further comprising:

a measurement terminating module for terminating measurement of respiratory cycles upon detection of three consecutive steady respiratory cycles or a timeout.

17. The apparatus according to claim 16, wherein the measurement terminating module further comprises:

an average time length calculating module for measuring time lengths of three latest respiratory cycles and calculating an average time length;

a judging module for terminating measurement of respiratory cycles if ratios of the time lengths of the three latest respiratory cycles to the average time length are all less than a preset threshold value; and a timeout interrupting module for terminating measurement of respiratory cycles if the measurement reaches a preset time limit.

18. A CT scanner comprising an apparatus for reducing radiation from CT measurement of respiratory cycles, the apparatus comprising:

a direction determining module for determining a lying direction of a patient to be measured, wherein the lying direction is a first direction or a second direction;

a tube position setting module for setting a position of a CT tube relative to the patient for a first respiratory cycle measurement of the patient to a first position if the lying direction is the first direction;

performing the first respiratory cycle measurement of the patient lying in the first direction with the CT tube at the first position;

setting the position of the CT tube relative to the patient for the first respiratory cycle measurement of the patient to a second position if the lying direction is the second direction; and performing the first respiratory cycle measurement of the patient lying in the second direction with the CT tube at the second position.

19. The CT scanner according to claim 18, wherein the tube position setting module further comprises a first tube position setting module for setting the CT tube to a position adjacent to the patient's right hand side.

20. The CT scanner according to claim 19, further comprising:

a second tube position setting module for setting the CT tube to a position adjacent to the patient's left hand side and executing a second respiratory cycle measurement, if the second respiratory cycle measurement is needed.

* * * * *